(12) United States Patent
Tepic

(10) Patent No.: US 10,357,241 B2
(45) Date of Patent: Jul. 23, 2019

(54) SUTURE ATTACHMENT APPARATUS

(75) Inventor: Slobodan Tepic, Zurich (CH)

(73) Assignee: Kyon AG, Zurich (CH)

( * ) Notice: Subject to any disclaimer, the term of this patent is extended or adjusted under 35 U.S.C. 154(b) by 30 days.

(21) Appl. No.: 13/265,019

(22) PCT Filed: Apr. 19, 2010

(86) PCT No.: PCT/US2010/031656
§ 371 (c)(1),
(2), (4) Date: Jan. 9, 2012

(87) PCT Pub. No.: WO2010/123835
PCT Pub. Date: Oct. 28, 2010

(65) Prior Publication Data
US 2012/0116451 A1 May 10, 2012

Related U.S. Application Data

(60) Provisional application No. 61/170,623, filed on Apr. 19, 2009.

(51) Int. Cl.
*A61B 17/04* (2006.01)
*A61B 17/06* (2006.01)

(52) U.S. Cl.
CPC .... *A61B 17/0401* (2013.01); *A61B 17/06166* (2013.01); *A61B 2017/044* (2013.01); *A61B 2017/0451* (2013.01); *A61B 2017/0619* (2013.01)

(58) Field of Classification Search
CPC ............ A61B 17/0401; A61B 17/0487; A61B 2017/0458; A61B 2017/0453; A61B 2017/0446; A61B 2017/045; A61B 2017/0454; A61B 2017/0451; A61B 2017/044; A61B 2017/0403; A61B 17/864; A61B 2017/042; A61B 2017/0422; A61B 2017/0424; A61B 2017/0425; A61B 2017/043; A61B 2017/0432; A61B 2017/0433; A61B 2017/0445; A61B 2017/0448; A61F 2/0811;
(Continued)

(56) References Cited

U.S. PATENT DOCUMENTS 3,766,610 A * 10/1973 Thorsbakken ................ 403/211
4,510,934 A * 4/1985 Batra ..................... A61B 17/06
428/377
4,656,806 A * 4/1987 Leibhard et al. ............... 52/704
(Continued)

FOREIGN PATENT DOCUMENTS

EP 2623066 8/2013
FR 2683715 11/1991
(Continued)

*Primary Examiner* — Christopher L Templeton
(74) *Attorney, Agent, or Firm* — Occhiuti & Rohlicek LLP

(57) ABSTRACT

A bone anchor has a central bore allowing for uniquely attaching a suture thereto. The bore is shaped so that it is wider at the bottom of the anchor than at the top of the anchor. A peg fits within the bore. The suture is looped around the peg and the peg is inserted into the bore. Friction between the bore, peg and suture holds the suture in place. A suture for use with the bone anchor may be formed by fusing together the ends of a plurality of fibers to form a loop.

9 Claims, 2 Drawing Sheets

(58) Field of Classification Search
CPC ...... A61F 2002/0864; A61F 2002/0858; A61F 2002/0847; A61F 2002/0841; A61F 2002/0817–0888
USPC ....... 606/232, 228, 65, 63, 321, 60, 301, 62, 606/300, 305, 307, 308, 319; 623/13.14, 623/13.11, 13.12, 13.2
See application file for complete search history.

(56) References Cited

U.S. PATENT DOCUMENTS

| | | | |
|---|---|---|---|
| 4,898,505 A * | 2/1990 | Froehlich | 411/55 |
| 5,268,001 A | 12/1993 | Nicholson et al. | |
| 5,336,240 A * | 8/1994 | Metzler et al. | 606/232 |
| 5,464,427 A | 7/1995 | Curtis et al. | |
| 5,480,403 A | 1/1996 | Lee et al. | |
| 5,571,139 A | 11/1996 | Jenkins, Jr. | |
| 5,575,819 A | 11/1996 | Amis | |
| 5,702,397 A * | 12/1997 | Goble et al. | 606/232 |
| 5,707,395 A * | 1/1998 | Li | 606/232 |
| 5,720,753 A * | 2/1998 | Sander et al. | 606/104 |
| 5,891,146 A | 4/1999 | Simon et al. | |
| 5,911,721 A * | 6/1999 | Nicholson et al. | 606/326 |
| 5,935,129 A | 8/1999 | Mcdevitt et al. | |
| 5,957,953 A * | 9/1999 | DiPoto et al. | 606/232 |
| 5,989,253 A * | 11/1999 | Bigliardi | 623/13.14 |
| 6,086,608 A * | 7/2000 | Ek et al. | 606/232 |
| 6,350,126 B1 * | 2/2002 | Levisman | A61C 8/0033 433/1 |
| 6,436,142 B1 * | 8/2002 | Paes et al. | 623/17.15 |
| 6,527,794 B1 | 3/2003 | McDevitt et al. | |
| 6,575,987 B2 * | 6/2003 | Gellman et al. | 606/151 |
| 6,585,730 B1 | 7/2003 | Foerster | |
| 6,616,694 B1 | 9/2003 | Hart | |
| 6,656,185 B2 * | 12/2003 | Gleason et al. | 606/74 |
| 6,923,824 B2 | 8/2005 | Morgan et al. | |
| 7,083,638 B2 * | 8/2006 | Foerster | 606/232 |
| 7,090,690 B2 * | 8/2006 | Foerster et al. | 606/232 |
| 7,147,652 B2 * | 12/2006 | Bonutti et al. | 606/232 |
| 7,172,595 B1 * | 2/2007 | Goble | 606/86 A |
| 7,217,279 B2 * | 5/2007 | Reese | 606/232 |
| 7,491,217 B1 * | 2/2009 | Hendren et al. | 606/232 |
| 7,828,820 B2 * | 11/2010 | Stone et al. | 606/232 |
| 7,976,565 B1 * | 7/2011 | Meridew | 606/232 |
| 8,133,258 B2 * | 3/2012 | Foerster et al. | 606/232 |
| 8,361,113 B2 | 1/2013 | Stone et al. | |
| 8,454,654 B2 * | 6/2013 | Ferragamo et al. | 606/232 |
| 8,523,902 B2 * | 9/2013 | Heaven et al. | 606/232 |
| 2003/0004545 A1 | 1/2003 | Burkhart et al. | |
| 2003/0195563 A1 * | 10/2003 | Foerster | 606/232 |
| 2004/0127907 A1 * | 7/2004 | Dakin | A61B 17/842 606/62 |
| 2004/0267360 A1 | 12/2004 | Huber | |
| 2005/0159812 A1 | 7/2005 | Dinger, III et al. | |
| 2005/0209639 A1 * | 9/2005 | Gidwani et al. | 606/228 |
| 2005/0216058 A1 * | 9/2005 | Egan et al. | 606/228 |
| 2005/0288762 A1 * | 12/2005 | Henderson et al. | 623/1.11 |
| 2006/0116685 A1 | 6/2006 | Urbanski et al. | |
| 2006/0135996 A1 * | 6/2006 | Schwartz et al. | 606/232 |
| 2006/0149258 A1 * | 7/2006 | Sousa | 606/72 |
| 2006/0235413 A1 * | 10/2006 | Denham et al. | 606/72 |
| 2006/0247642 A1 * | 11/2006 | Stone et al. | 606/73 |
| 2006/0265010 A1 * | 11/2006 | Paraschac et al. | 606/232 |
| 2007/0038221 A1 * | 2/2007 | Fine et al. | 606/73 |
| 2007/0118217 A1 | 5/2007 | Brulez et al. | |
| 2007/0203498 A1 * | 8/2007 | Gerber et al. | 606/72 |
| 2007/0225719 A1 * | 9/2007 | Stone et al. | 606/72 |
| 2008/0234758 A1 * | 9/2008 | Fisher et al. | 606/309 |
| 2008/0249567 A1 * | 10/2008 | Kaplan | 606/232 |
| 2008/0288070 A1 * | 11/2008 | Lo | 623/13.14 |
| 2009/0012522 A1 | 1/2009 | Lob | |
| 2009/0234451 A1 | 9/2009 | Manderson | |
| 2009/0292321 A1 | 11/2009 | Collette | |
| 2010/0318188 A1 | 12/2010 | Linares | |
| 2011/0046733 A1 * | 2/2011 | Eggli | 623/13.14 |
| 2011/0066185 A1 | 3/2011 | Wotton, III | |
| 2013/0345747 A1 | 12/2013 | Dreyfuss | |

FOREIGN PATENT DOCUMENTS

| | | | |
|---|---|---|---|
| GB | 2084468 | 4/1985 | |
| WO | WO93/21857 | 11/1993 | |
| WO | WO 95/00318 | 1/1995 | |
| WO | WO95/15726 | 6/1995 | |
| WO | WO 97/00766 | 1/1997 | |
| WO | WO02/17795 | 3/2002 | |
| WO | WO 2007/147634 | * 12/2007 | A61F 2/08 |
| WO | WO 2008/131370 | 10/2008 | |
| WO | WO2010/123835 | 10/2010 | |
| WO | WO2012/145275 | 10/2012 | |

* cited by examiner

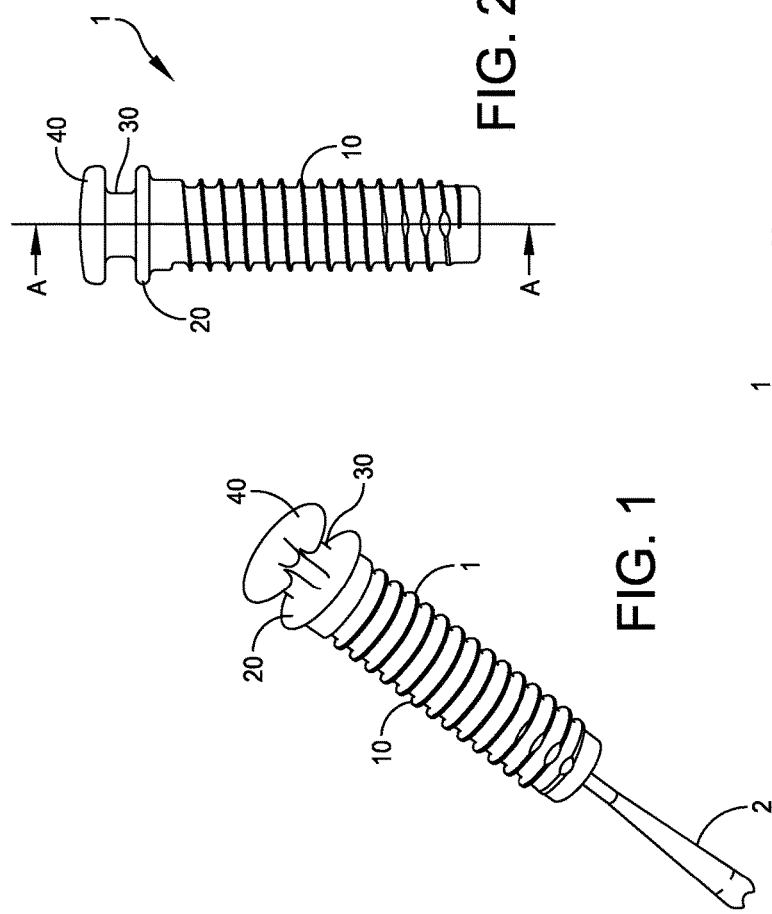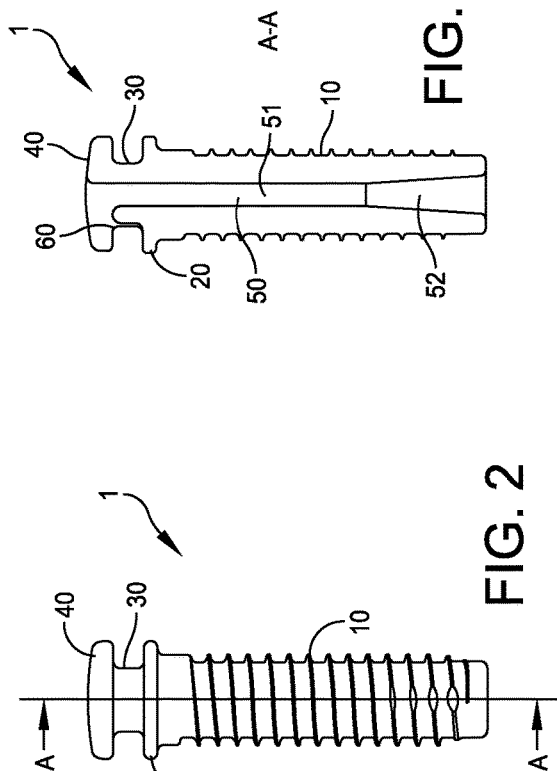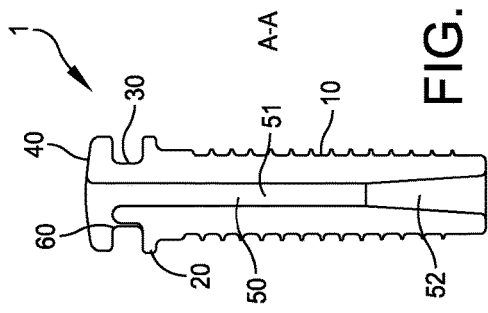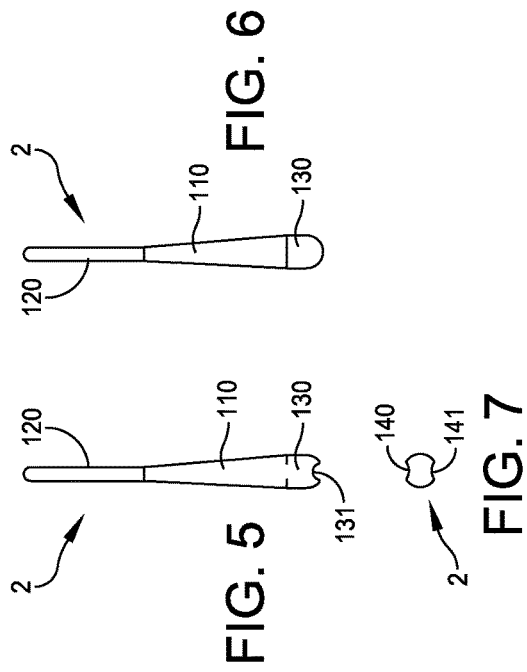

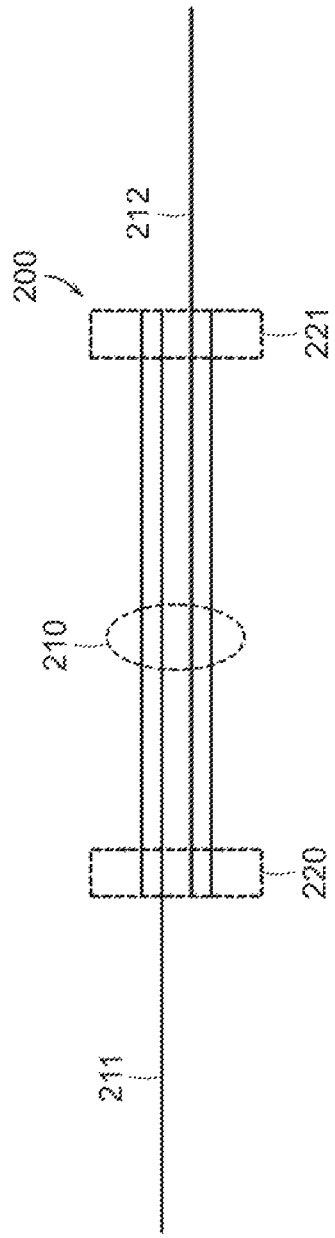
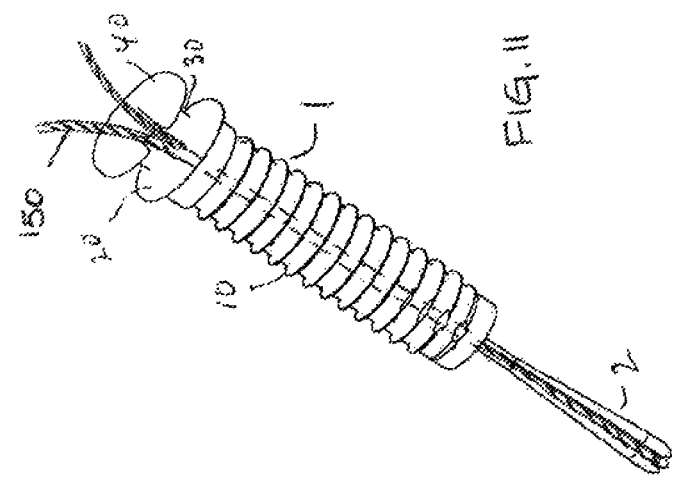
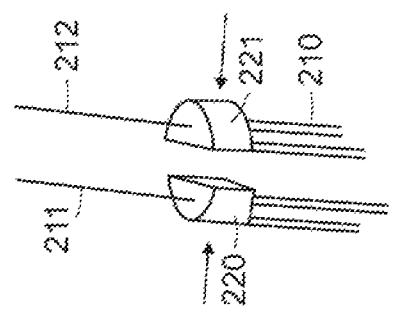
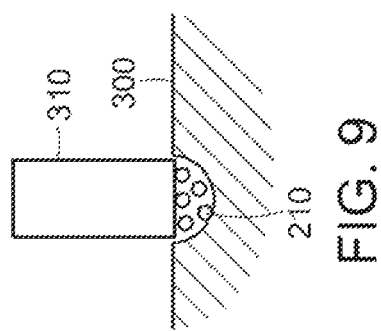

SUTURE ATTACHMENT APPARATUS

CROSS-REFERENCE TO RELATED APPLICATIONS

The present application is a U.S. national phase application, filed in accordance with 35 U.S.C. § 371, of International Application No. PCT/US2010/031656, which was filed Apr. 19, 2010, and which claims the benefit of the filing date of U.S. Provisional Application No. 61/170,623, which was filed Apr. 19, 2009. The content of these priority applications is hereby incorporated by reference herein in its entirety.

TECHNICAL FIELD (FIELD OF THE INVENTION)

The present invention relates to a bone screw and a method and apparatus for attaching sutures to a bone screw or bone anchor. More particularly, it relates to a method and apparatus for attaching a suture to a bone screw or bone anchor having a central hole.

BACKGROUND OF THE INVENTION

There are a variety of anchors used to fix the ends of an ACL prosthesis into bones. Most commonly, they are so-called interference screws, designed to be inserted along the prosthesis (transplanted tendon or ligament, or an artificial ligament) within an anchor hole, or tunnel, drilled in the bone. The interference screw jams the prosthetic tissue against the bone within the anchor hole. Another common technique is so-called cross-pin used to anchor a loop of the prosthetic tissue within a hole drilled in the femoral condyle. In all cases, prosthetic tissue exits the tunnel by bending over the edge of the bone; healing/remodeling of the bone is expected to fill the gaps and to result in a natural-like anchorage of the ligament in the bone. Neither of these techniques is suitable for a permanent anchorage of an artificial ACL replacement. Bending of the prosthesis over the edge of the hole will lead to both, bone loss due to contact resorption and mechanical damage—ultimately failure—of the prosthesis due to bending and wear at the edge of the hole.

The present inventor has an improved apparatus and method for fixing the ends of an ACL prosthesis. The bone anchor is disclosed in U.S. patent application Ser. No. 12/107,070 filed on Apr. 21, 2008. The bone anchor includes a central hole through which the ACL prosthesis is passed. A knot is tied in the end of the ACL prosthesis to retain it within the central hole. The central hole is sized to prevent the knot from pulling through. However, sometimes the knot may pass through the central hole causing the ACL prosthesis to loosen or fail. Additionally, tying the knot can be difficult while retaining the ACL prosthesis taut. Accordingly, an improved method for retaining the ACL prosthesis within the central hole would be advantageous.

Additionally, a bone screw may be used for attaching a suture to bone for other purposes. A lateral suture screw for attaching a suture is disclosed in U.S. patent application Ser. No. 12/107,071 filed on Apr. 21, 2008 by the present inventor. The lateral suture screw includes a post extending above the screw. An attachment hole is formed in the head of the post for attaching the suture. The suture is connected to the attachment hole with a knot. As with the bone anchor the knot may pull through the attachment hole. Therefore, a need exists for an improved suture screw and mechanism for attaching the suture to the screw.

DISCLOSURE OF INVENTION

According to one aspect of the invention, a lateral suture screw includes a central axis hole. The lateral suture screw includes a post extending above the screw and a head above the post. The head includes a slot between the central axis hole and the post. A suture is connectable within the central axis hole.

According to another aspect of the invention, the central axis hole is shaped to retain the suture therein. A first portion of the central axis hole is cylindrical with parallel sides; a second portion has angled sides. According to another aspect of the invention, a bone anchor for an ACL prosthesis has a central axis hole shaped to retain the ACL prosthesis therein. A first portion of the central axis hole is cylindrical with parallel sides; a second portion has angled sides.

A peg is insertable within the central axis hole. According to an aspect of the invention, the peg is shaped similarly to the interior of the central axis hole. According to another aspect of the invention, the peg has indented sides to accommodate the suture.

According to another aspect of the invention, the suture is looped around the peg. The suture is passed through the central axis hole of the screw and the peg is pulled within the central axis hole. The peg holds the suture within the central axis hole. According to another aspect of the invention, the ends of the suture are passed through a central axis hole of a bone screw. A peg is inserted into the central axis hole between the ends of the suture. The peg holds the suture within central axis hole. According to another aspect of the invention, the ends of the suture are tied in a knot around the peg. The knot retains the suture and peg in place.

According to another aspect of the invention, a suture is formed for use with the bone screw and peg of the present invention. According to an aspect of the invention, the suture is formed into a loop. The filaments are fused together to maintain the loop of the suture. According to another aspect of the invention, one or more filaments are longer than the remaining filaments. The filaments are fused so that the longer filaments extend beyond the fused portion.

DESCRIPTION OF THE DRAWINGS

FIG. 1 is a perspective view of a bone screw and peg according to an embodiment of the present invention.

FIG. 2 is a side view of a bone screw according to an embodiment of the present invention.

FIG. 3 is a cross sectional view of a bone screw according to an embodiment of the present invention.

FIG. 4 is a top view of a bone screw according to an embodiment of the present invention.

FIGS. 5-6 are side views of a peg according to an embodiment of the present invention.

FIG. 7 is an end view of a peg according to an embodiment of the present invention.

FIG. 8 is side view of formation of a suture according to an embodiment of the present invention.

FIG. 9 is an end view of a device for forming a suture according to an embodiment of the invention.

FIG. 10 is a side view of formation of formation of a suture according to an embodiment of the invention.

FIG. 11 is a perspective view of a bone screw and peg, with a suture abutting the bottom of the peg, according to an embodiment of the present invention.

BEST MODE FOR CARRYING OUT THE INVENTION

FIG. 1 illustrates a bone screw or anchor 1 and peg 2 for holding a suture according to an embodiment of the present invention. FIGS. 2-4 are various views of bone screw. FIGS. 5-7 are various views of the peg.

The bone screw 1 of the present invention allows for attachment of a lateral suture. The bone screw includes a body 10 having threads thereon. The body 10 can be threaded into a hole drilled into a bone. A suture can be attached to the bone screw 1 as set forth herein. At the top of the body 10 is a base 20. When screwed into the bone, the base 20 abuts the surface of the bone. A post 30 extends from the base 20. A head 40 is positioned on the post opposite the base 30. The base 20 and head 40 have a diameter wider than the post 30. The suture wraps around the post 30 and is held in place by the base 20 and head 40. A central axis hole 50 extends within the head 40, post 30, base 20 and body 10 of the screw 1. A slot 60 is formed in the head 40 from the central axis hole to the edge of the head 40. The suture is positioned within the central axis hole 50 and the slot 60 so that it can extend around the post 30 between the head 40 and the base 20.

The central axis hole 50 is shaped to retain the suture therein. The central axis hole 50 includes a first portion 51 which is cylindrical having parallel sides. The first portion 51 of the central axis hole 50 is sized to accommodate the size of the suture. A second portion 52 of the central axis hole 50 has angled sides. The angled sides of the second portion 52 are wider at the outside end than at the first portion 51.

A peg 2 can be positioned within the central axis hole 52 to hold the suture in place. An embodiment of the peg is illustrated in FIGS. 5-7. FIGS. 5 and 6 are perpendicular side views of the peg 2. The peg 2 includes three portions. A first portion 120 is substantially cylindrical. It is narrower than the first portion 51 of the central axis hole 50. A second portion 110 of the peg 2 has a circular cross section with angled sides. A third portion 130 is rounded. It includes an indentation 131 in one direction. The suture can fit within the indentation 131. FIG. 7 is a end view of the third portion 130 of the peg 2. Indentations 140, 141 on the sides of the peg 2 correspond to the indentation 131 in the end. The suture is positioned around the peg within the indentations 131, 140, 141. The suture is looped around the peg 2 and inserted within the central axis hole 50 of the screw 1. When the suture is pulled within the screw 1, it pulls the peg 2 into the central axis hole 50 of the screw 1. The peg 2 holds the suture in place. Friction between the central axis hole 50, peg 2 and suture keeps the suture in place.

FIGS. 8-9 relate to formation of a suture 200 for use with the screw 1 and peg 2 of the present invention. The suture 200 made from a plurality 210 of high performance polymeric fibers. According to one aspect of the invention, the suture is formed of a plurality of independent filaments or fibers. Such fibers may include oriented, high modulus, ultra high molecular weight polyethylene available from either DSM, Netherlands as DYNEEMA, or from Honeywell, USA as SPECTRA. A plurality of fibers 210 are positioned together. According to an embodiment of the invention, two of the fibers 211, 212 are longer than the other fibers and extend past the others. One fiber may be longer in both directions. According to an embodiment of the invention, the fibers have length of approximately 300-500 mm. The longer fibers extend approximately 300 mm past the ends of the other fibers.

The fibers are fused together at their ends 220, 221. To fuse the fibers, each end is fused in a semi-circle. FIG. 9 illustrates a device for fusing the ends. The device includes a base 300 having a semi-circular indentation therein. A press 310 fits within the indentation. An end 220, 221 of the fibers 210 is positioned within the indentation. The end is heated, to approximately 143 degrees C. and pressed in order to fuse them together. Once both ends have been fused, a loop is made in the suture. The two ends 220, 221 are fused together as illustrated in FIG. 10. Once fused, the suture is in the form of a loop fused at its end. Extensions are positioned beyond the fused portions. To use the suture, the extensions 211, 212 can be passed through the central axis hole 50 of the screw. The extensions 211, 212 are used to pull the suture into the hole. The peg 2 can be positioned within the suture loop. For the other end of the suture, the extensions are again passed through a central axis hole of the screw. When the suture is pulled taut, a peg 2 is pressed into the central axis hole to hold the suture in place. Friction retains the suture and peg in place. The ends of the suture may be tied in a knot below the peg to help retain the suture in place.

FIG. 11 is identical to FIG. 1 except that FIG. 11 also illustrates a suture 150 having a loop abutting the end of the peg.

Having disclosed at least one embodiment of the present invention, various adaptations, modifications, additions, and improvements will be readily apparent to those of ordinary skill in the art. Such adaptations, modifications, additions and improvements are considered part of the invention which is only limited by the several claims attached hereto.

What is claimed is:

1. A bone anchor assembly for attaching a suture, the assembly comprising:
   an anchor having a top, a bottom, and a central axis therebetween, wherein the anchor comprises a threaded body, a base that extends from the body towards the top of the anchor and abuts a surface of a bone when the anchor is screwed into the bone, and a bore extending through the anchor along the central axis, the bore being narrower towards the top of the anchor and wider towards the bottom of the anchor; and
   an elongated peg, inserted in the bore, comprising a narrower first end that resides towards the top of the anchor and a wider second end having an indentation that receives and holds a looped suture at a bottom end of the anchor;
   wherein the anchor includes a head structure at the top of the anchor, the head structure comprising a post defining a circumferential channel, wherein the head structure further defines a slot extending from the bore to the circumferential channel, wherein the looped suture extends from the bore via the slot, and is wrapped around the post defining the circumferential channel.

2. The bone anchor assembly of claim 1, wherein the bore comprises:
   a first portion towards the top of the anchor, the first portion having a length and being cylindrical with substantially constant diameter along the length of the first portion; and
   a second portion towards the bottom of the anchor, the second portion being wider towards the bottom of the anchor than towards the top of the anchor.

3. The bone anchor assembly of claim 2, wherein the peg comprises:
   a first portion towards the first end of the peg, the first portion of the peg having a length and being cylindrical with substantially constant diameter along the length of the first portion of the peg; and a second portion towards the second end of the peg, the second portion of the peg being wider towards the second end of the peg than towards the first end of the peg.

4. The bone anchor assembly of claim 1, wherein the looped suture abuts the second end of the peg and the suture extends through the bore of the anchor.

5. The bone anchor assembly of claim 4, wherein the suture is formed of a plurality of fibers, the fibers having ends.

6. The bone anchor assembly of claim 5, wherein the plurality of fibers are fused together at the ends thereof.

7. The bone anchor assembly of claim 1, wherein the post extends from the base to a head, wherein the post, the base, and the head each have a diameter and the diameter of the base and the head are wider than the diameter of the post; and wherein the head has the slot formed therein extending from the bore to an edge of the head.

8. The bone anchor assembly of claim 1, wherein the looped suture comprises a bundle of fibers fused at a loop closing point defining a loop formed from the bundle of fibers, with at least some fibers of the bundle of fibers comprising fiber sections extending outside the loop.

9. The bone anchor assembly of claim 8, wherein the looped suture comprises two fused sub-portions formed from fusing the bundle of fibers at two separate locations, with the two fused sub-portions being fused together at the loop closing point defining the loop.

* * * * *